United States Patent [19]
Mihalko et al.

[11] Patent Number: 5,340,587
[45] Date of Patent: Aug. 23, 1994

[54] LIPOSOME/BRONCHODILATOR METHOD & SYSTEM

[75] Inventors: Paul J. Mihalko, Fremont; Robert M. Abra, San Francisco; Ramachandran Radhakrishnan, Fremont, all of Calif.

[73] Assignee: Liposome Technology, Inc., Menlo Park, Calif.

[21] Appl. No.: 366,299

[22] Filed: Jun. 13, 1989

Related U.S. Application Data

[63] Continuation of Ser. No. 22,669, Mar. 19, 1987, abandoned, which is a continuation-in-part of Ser. No. 737,221, May 19, 1985, abandoned, Ser. No. 860,528, May 7, 1986, abandoned, and Ser. No. 937,607, Dec. 3, 1986, abandoned.

[51] Int. Cl.$^5$ .................. A61K 9/127; A61K 9/42
[52] U.S. Cl. .................. 424/450; 252/305; 424/45; 514/826; 514/930; 514/958
[58] Field of Search .......... 252/305; 428/402.2; 424/45, 450; 436/829; 514/826, 930, 958

[56] References Cited

U.S. PATENT DOCUMENTS

| | | | |
|---|---|---|---|
| 3,322,625 | 5/1967 | Shimmin | 424/45 |
| 3,594,476 | 7/1974 | Merrill | 252/305 X |
| 3,933,822 | 1/1976 | Broughton et al. | 424/45 X |
| 4,211,771 | 7/1980 | Witkowski et al. | 514/43 |
| 4,232,002 | 11/1980 | Nogrady | 424/45 |
| 4,235,871 | 11/1980 | Papahadjopoulos et al. | 428/402.2 X |
| 4,438,052 | 3/1984 | Weder et al. | 514/2 X |
| 4,608,211 | 8/1986 | Handjani et al. | 428/402.2 X |
| 4,699,995 | 10/1987 | Buckle | 560/61 |

FOREIGN PATENT DOCUMENTS

| | | |
|---|---|---|
| 0084898 | 1/1983 | European Pat. Off. |
| 3430385 | 3/1985 | Fed. Rep. of Germany |
| WO86/01714 | 3/1986 | PCT Int'l Appl. ........... 424/450 |
| 2145107 | 3/1985 | United Kingdom ........... 424/45 |

*Primary Examiner*—Richard D. Lovering
*Attorney, Agent, or Firm*—Peter J. Dehlinger

[57] ABSTRACT

A method and system for treating bronchial constriction. The system includes a liposome composition containing a $\beta_2$-adrenoreceptor agonist in a liposome-entrapped form, and a device for aerosolizing a metered quantity of the composition. The drug in liposome aerosol form is substantially more effective in bronchodilation, over a substantially longer time, than the same amount of drug in free-drug aerosol form.

7 Claims, 4 Drawing Sheets

LIPOSOME/BRONCHODILATOR METHOD & SYSTEM

This application is a continuation of U.S. patent application for "Liposome/Bronchodilator Method and System", Ser. No. 07/022,669 filed Mar. 6, 1987, now abandoned, which is a continuation-in-part of U.S. patent application for "Liposome Inhalation Method and System," Ser. No. 737,221, filed May 22, 1985 and now abandoned; "Liposome Concentrate and Method", U.S. Ser. No. 860,528, filed May 7, 1986 and now abandoned; and "Liposome Inhalation Method and System", U.S. Ser. No. 937,607, filed Dec. 3, 1986 and now abandoned.

1. FIELD OF THE INVENTION

The present invention relates to drug delivery by inhalation, and, in particular, to an improved delivery system and method for treating bronchial constriction by a liposome-entrapped $\beta_2$-agonist.

2. REFERENCES

The following references are incorporated herein by corresponding number:
1. *Remington's Pharmaceutical Sciences*, (Gannaro, A. R., Ed.), 17th edition, Mack Publishing Company (1985).
2. Szoka, F., Jr., et al, *Ann Rev Biophys Bioeng* (1980), 9: 467.
3. Szoka, F., Jr., et al, *Proc Natl Acad Sci (USA)* (1978) 75: 4194.
4. Hollenbeck, R. G., et al, in "Pharmaceutics and Pharmacy Practice" (Banker, G. S., et al, eds), J. P. Lippincott, Philadelphia (1982), pp. 382–391.
5. Amdur, M. D., et al, *Am J Phys Soc* 912: 364 (1958).
6. Pawlak, et al, *Acta Polon Pharm* 27(5): 453 (1970).

3. BACKGROUND AND SUMMARY

Inhalation provides an effective means for treating a variety of bronchial constriction diseases, such as bronchial asthma, emphysema, bronchitis, and bronchiectasis. An obvious advantage of inhalation in treating bronchial constriction is the ability to deliver the drug directly to the site of drug action. A related advantage is the rapid onset of the therapeutic effect, compared with other routes of administration, such as intramuscular and oral routes. For drugs which are susceptible to breakdown in the gastrointestinal tract, or which otherwise cannot be administered orally, inhalation may be preferred for a variety of reasons over intravenous or intramuscular injection.

Bronchial constriction conditions or diseases are treated with a bronchodilator drug, such as albuterol, epinephrine, isoetharine, isoproteranol, metaproteranol, terbutaline, and salbutamol, which have strong or moderate $\beta_2$-adrenoreceptor agonist activity (1), in general, these compounds are uncharged, water-soluble, and relatively small molecules. An aqueous solution of a $\beta_2$-agonist drug may be administered in aerosolized form from a pneumatic or ultrasonic nebulizer. Alternatively, the drug can be suspended in micronized form in a fluorocarbon propellant solvent, and delivered in metered dose from a pressurized cannister. Following aerosolization, most of the propellant solvent is lost through flash evaporation and replaced by moisture in the respiratory tract, leading to the deposition of hydrated micronized particles.

Both types of inhalation systems mentioned above are based on delivery of the drug in a free form to sites in the respiratory tract. As such, the drug is rapidly utilized and also in the case of pulmonary deposition, rapidly absorbed into the bloodstream. Because of the rapid drug uptake and utilization, it is generally necessary to administer the drug at frequent intervals to maintain a desired therapeutic dose level at the site of action. Rapid uptake into the bloodstream also limits the amount of drug that can be administered safely with each administration. $\beta$-adrenergic agonists generally produce some degree of tachycardia and dizziness, and even at relatively low dose levels, these stimulatory effects are unpleasant to the patient. An additional problem associated with administration of micronized particles is the irritation that these particles may produce in the respiratory tract.

A variety of methods and apparatus which are designed to produce liposome-based aerosols, for drug delivery by inhalation, have been proposed heretofore. UK patent application GB 2,145,107A describes an aerosol device which brings aqueous and organic-solvent phase solutions together under pressure, and passes the mixture through a nozzle to form aerosolized liposomes. EPO patent application 0,158,441 discloses liposome formation, in aerosol form, from a water/lipid/ethanol mixture. In PCT application WO 86/01714, it is proposed to spray lipid droplets in a volatile liquid carrier, with liposome formation occurring upon contact of the droplets with a moist aqueous surface. UK patent application GB 2,170,815 describes a system in which an aqueous solution is emulsified in a lipid-containing propellant solvent, then sprayed through an atomizing nozzle to form lipid-coated droplets which can form liposomes upon contact With a moist surface. All of these approaches are characterized by "in situ" liposome formation, and as such, the concentration and size of the liposomes formed, and the percentage of drug entrapment in the liposomes will vary from one dose delivery to another, depending upon temperature, extent of solvent mixing, and the total and relative amounts of solvent components present in the system. Thus each of these systems would be difficult to adapt for metered dose delivery, where a reproducible amount of liposome-encapsulated drug is needed.

Further, although the above disclosures indicate that a variety of drugs, including bronchodilators, may be delivered in liposomal form, none of the references demonstrate how or whether liposome drug delivery effects the pharmacokinetic action of a liposome-entrapped drug in the respiratory tract. In particular, it is not known from these earlier references how liposomes behave in the respiratory-tract environment, how $\beta_2$-agonist activity would be effected by the presence of liposomal lipids, and whether liposomes can significantly modulate drug release and side effects observed with $\beta_2$-agonist, particularly at low drug dosage.

4. SUMMARY OF THE INVENTION

Co-pending patent application for "Liposome Inhalation Method and System" U.S. Ser. No. 737,221, filed May 22, 1985 and now abandoned, discloses a liposome-based aerosol system for delivering a drug, at a controlled release rate, via the respiratory tract. The invention is based on two discoveries: First, that initial systemic-uptake spiking effects due to initial systemic uptake of drugs from the site of administration in the respiratory tract can be eliminated or greatly reduced by administering the drug in a predominantly liposome-encapsulated form. Secondly, it was found that the rate of release of a water-soluble drug from a drug/liposome composition delivered to the respiratory tract can be modulated over a wide range, according to the acyl-chain composition of the phospholipids making up the liposomes. As a rule, slower drug release rates correlate with longer in vitro drug efflux half lives in serum. The liposome aerosol compositions used in these studies were prepared under conditions in which the drug was predominantly in liposome-encapsulated form, and the liposome suspensions were delivered in metered dose form from a fixed-volume nebulizer.

Co-pending patent application for "Liposome Concentrate and Method", U.S. Ser. No. 860,528, filed May 7, 1986 and now abandoned, addresses another aspect of effective drug delivery in a liposome-based inhalation system: that of delivering a water-soluble, liposome-permeable drug in predominantly encapsulated form, from a dilute aqueous liposome suspension. The method of the invention involves preparing and storing a liposome/drug suspension initially in paste form, then diluting the paste to a concentration suitable for aerosolizing.

Co-pending U.S. patent application Ser. No. 937,607, filed Dec. 3, 1986 now U.S. Pat. No. 4,737,323, additionally showed that administration of the $\beta_2$-agonist metaproteranol sulfate (MPS) in liposomal form via inhalation reduced initial plasma levels of the drug more than about 8 fold with respect to free drug, and that plasma levels remained substantially constant over a two hour period, compared with a rapid drop in plasma levels of the drug administered by inhalation in free form. At the levels of MPS which were studied, the percent protection against bronchoconstriction provided by the drug was about the same for both free drug and liposomal-entrapped drug.

It has now been discovered, according to one aspect of the present invention, that by encapsulating $\beta_2$-adrenoreceptor agonists in liposome-entrapped form, and administering the liposome-drug composition in metered form, at a therapeutic drug dose (i.e., minimum dose required for optimal or near-optimal short-term therapeutic effect), that $\beta_2$-agonists produce significantly greater bronchodilation, over an extended time period, than is produced by the the same amount of $\beta_2$-agonist delivered to the respiratory tract in a free-drug aerosol form.

The system of the invention includes a liposome composition containing a $\beta_2$-adrenoreceptor agonist in liposome-entrapped form, and a device for aerosolizing, in a form suitable for inhalation, a metered quantity of the composition. The metered drug quantity contains an amount of liposome-entrapped $\beta_2$-agonist which, when delivered to the respiratory tract in aerosol form, produces a substantially greater degree of bronchodilation 1-2 hours after drug administration than is produced by the the same amount of $\beta_2$-agonist delivered to the respiratory tract in a free-drug aerosol form.

In one preferred embodiment, the liposome position contains the $\beta_2$-agonist predominantly in liposome-entrapped form. The rate of release of drug from the liposomes may be modulated according to the acyl-chain composition of the lipids forming the liposomes.

In one delivery device, the liposome composition is a liposome paste in which more than 50% of the aqueous phase is encapsulated within the liposomes. The delivery device includes a mixing chamber in which a measured volume of paste is mixed with at least 1-2 volumes of aqueous medium immediately before aerosolization. In a second delivery device, the liposome composition includes a suspension of spray-dried liposomes in a propellant solvent. The delivery device is a pressurized cannister containing the suspension under pressure, and a valve for releasing a selected volume of the suspension in aerosolized form.

In the method of the invention, a liposome composition of the type described above is administered by aerosolizing, in a form suitable for inhalation. The liposome-entrapped drug is administered in a metered dose containing an amount of liposome-entrapped $\beta_2$-agonist which, when delivered to the respiratory tract in a liposome aerosol form, produces substantially greater bronchodilation, 1-2 hours after drug administration, than is produced by the the same amount of $\beta_2$-agonist delivered to the respiratory tract in a free-drug aerosol form.

These and other objects and features of the present invention will become more fully apparent when the following detailed description of the invention is read in conjunction with the accompanying drawings.

DETAILED DESCRIPTION OF THE INVENTION

1. Liposome Suspension

Figure 1A:
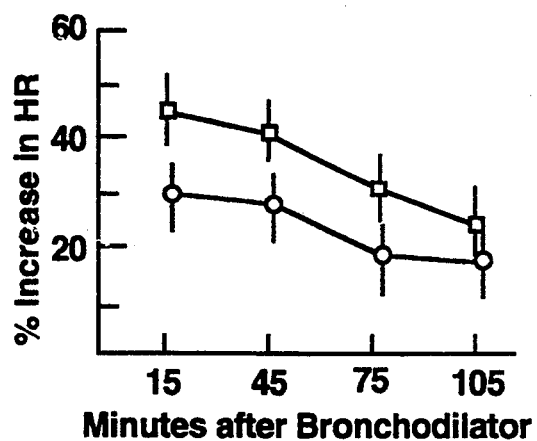
FIGS. 1A and 1B are plots showing percent increase in heart rate in test subjects following treatment with free MPS (open squares in the figures), and MPS encapsulated in liposomes with relatively high (1A) and low (1B) rates of drug release.

The preferred liposome composition of the present invention is formulated to contain (a) the $\beta_2$-agonist drug predominantly in liposome-entrapped form, and (b) a lipid composition designed to produce a desired drug-release rate when the liposomes are administered to the respiratory tract. Section IA below considers the relationship between liposome bilayer components and drug-release rates. Section IB describes methods for preparing liposomes containing entrapped drugs. Methods of forming liposome compositions containing a drug in predominantly liposome-entrapped form are discussed in Sections IC and ID.

A. Lipid Components and Drug Release Rates

In studies conducted in support of the present invention and reported in Examples I–III, the effects of lipid acyl chain length and degree of unsaturation, lipid charge, and presence of sterol on in vitro drug efflux rates from liposomes were examined. Of factors which were studied, the most important is acyl chain length and the degree of unsaturation in the phospholipid(s) forming the liposomes. The study reported in Example I shows that the in vitro drug efflux half life (a measure of the time required for one-half of the liposome-entrapped drug to be released from the liposomes on incubation in vitro) can vary over a hundredfold or more, according to acyl chain length and degree of unsaturation. In forty different lipid mixtures which were studied, increasing either acyl chain length, or the degree of saturation of phospholipid acyl chains, led to greater drug efflux half lives, with the most significant increases being observed when the liposomes included a significant proportion of lipids whose transition temperature ($T_c$) are above the temperature at which the efflux half lives are measured, e.g., 37° C.

Studies on the effect of lipid charge on drug efflux rates, reported in Example II, indicate that the addition of a negatively charged lipid, such as phosphatidylglycerol (PG), at a mole ratio of about 10%, produces a slight to moderate increase in drug half life. The lipid-charge Effect is dependent somewhat on the degree of saturation and chain length in the charged and uncharged lipids used in forming the liposomes, with the charged lipid producing a greater increase in drug half life where the liposomes are formed of predominantly shorter and/or unsaturated lipids, and producing less effect in the case of longer-chain and/or saturated lipids.

The effect of sterol, either cholesterol or the negatively charged cholesterolhemisuccinate, on drug efflux from liposomes is considered in Example III. An initial study involved liposomes formed with one of eight PC lipids or lipid mixtures and cholesterol, at a PC/cholesterol mole ratio of 60:40. In general, cholesterol was found to have a moderating effect on the acyl composition of the phospholipid, slightly increasing drug half lives in liposomes containing predominantly unsaturated and shorter-chain length PCs, and producing a significant decrease in the drug half lives in liposomes containing predominantly longer-chain and more saturated phospholipids. This moderating effect may be due to the known effect of cholesterol in decreasing the fluidity of unsaturated membranes (which would produce greater efflux half lives) and increasing the fluidity of saturated membranes (which would produce shorter half lives).

A negatively charged sterol, such as cholesterol hemisuccinate, when formulated with uncharged phospholipid(s), appears to have little effect on drug efflux rates over that observed in liposomes formed from uncharged phospholipids and cholesterol (Example III). Surprisingly, however, the drug half lives observed in liposomes composed of uncharged phospholipids and cholesterol are enhanced significantly by the addition of negatively charged phospholipid (10 mole percent PG). As seen from the data presented in Table 5 of Example III, in nearly all of the PC mixtures which were studied, the addition of 10 mole percent PG to liposomes also containing PC (50 mole percent) and cholesterol (40 mole percent) enhanced the drug half life more than twofold, and in some cases more than threefold over those observed for liposomes composed of PC and cholesterol only. The combination of a neutral phospholipid, such as PC, a charged phospholipid, such as PG, and cholesterol appears particularly advantageous in achieving a range of drug half lives, as measured at 37° C., of between about 2 and 24 hours.

The lipids forming the liposomes may, of course, include phospholipids and sterols other than the model lipids used in the above-mentioned studies, and may also include other types of lipids, such as glycolipids and sphingolipids, which are compatible with liposome formation. A list of lipids which are used commonly in liposome formation is given on page 471 of reference 2. The liposomes may also be formulated to include various types of drug-protective or lipid-protective agents, such as the antoxidant α-tocopherol, which was typically included at a 1.0 mole percent in the liposomes described herein.

The studies lust described, and reported in detail in Examples I–III were carried out with the $\beta_2$-agonist metaproteranol sulfate (MPS), a water-soluble, liposome-permeable drug. The results also apply to other $\beta_2$-agonists, such as albuterol (salbutamol) sulfate, ephidrine sulfate, ephidrine bitartrate, isoetharine hydrochloride, isoetharine mesylate, isoproteranol hydrochloride, isoproteranol sulfate, metaproteranol sulfate, terbutaline sulfate, procaterol, and bitolterol mesylate, which are water soluble, uncharged, and about the same size as MPS.

Where the liposomes are prepared for suspension, in spray-dried form, in a propellant solvent, it is also advantageous to select lipids whose phase transition is above the drying temperature used in spray drying. As a rule, drying temperatures of at least about 37° C. and preferably above about 40° C. are used for spray drying. Accordingly, lipid components, such as phosphatidylcholine (PC), used in liposome preparation will contain partially or largely saturated acyl-chain moieties. Methods for spray drying liposomes are given in Section ID below.

B. Liposome Preparation

The liposomes may be prepared by a variety of techniques, such as those detailed in reference 2. One preferred method for preparing drug-containing liposomes is the reverse phase evaporation method described in reference 3 and in U.S. Pat. No. 4,235,871. In this method, a solution of liposome-forming lipids is mixed with a smaller volume of an aqueous solution of the $\beta_2$-agonist drug, and the mixture is dispersed to form a water-in-oil emulsion. After removing the lipid solvent by evaporation, the resulting gel is converted to liposomes, with an encapsulation efficiency, for a water-soluble drug, of up to 50%. The reverse phase evaporation vesicles (REVs) have typical average sizes between about 2–4 microns and are predominantly oligolamellar, that is, contain one or a few lipid bilayer shells. The oligolamellar nature of the vesicles may facilitate drug efflux and thus contribute to a lower efflux half life for an encapsulated drug.

A simple lipid-hydration procedure for producing multilamellar vesicles (MLVs) may be preferred where high drug encapsulation efficiency is not desired. In this procedure, a mixture of liposome-forming lipids dissolved in a suitable solvent is evaporated in a vessel to form a thin film, which is then covered by an aqueous solution of the drug. The lipid film hydrates to form MLVs, typically with sizes between about 0.1 to 10 microns. As in the REV method, the $\beta_2$-agonist drug to be encapsulated is contained in the hydrating medium, and is encapsulated upon formation of the liposomes.

Following liposome preparation, the dispersion can be treated by extrusion to reduce overall liposome size and particle size heterogeneity. Reducing liposome particle size may be important in achieving efficient aerosolization of the liposomes, and in maximizing drug deposition in a desired portion of the respiratory tract. Experiments conducted in support of the present invention indicate that liposomes contained in an aqueous suspension may be aerosolized efficiently in the form of liposome-containing aqueous particle mist, where the liposomes are predominantly less than about 1 micron in diameter. In terms of targeting the liposomes to a particular region of the respiratory tract, it is advantageous to produce liposomes whose sizes are compatible with a desired size range of mist particles. For example, mist particle sizes of greater than about 5 microns would favor deposition in the upper respiratory-tract regions, and particle sizes of between about 0.5–1.5 microns would favor deposition in lower pulmonary regions of the respiratory tract. Generally liposomes having particle sizes less than about 1 micron are compatible with a wide range of mist particle sizes, e.g., from 1–10 microns. As will be seen below, where the liposomes are aerosolized in the form of an aqueous mist, the actual sizes of particles carrying the liposomes may be much greater than that of the liposomes themselves, and thus actual liposome size becomes less crucial to targeting.

One effective sizing method involves extruding an aqueous suspension of the liposomes through a polycarbonate membrane having a selected uniform pore size, typically 0.2, 0.4, 0.6, 0.8 or 1 micron (reference 3). The pore size of the membrane corresponds roughly to the largest sizes of liposomes produced by extrusion through that membrane, particularly where the preparation is extruded two or more times through the same membrane. This method of liposome sizing is used in preparing the liposomes described in the several examples below. A more recent method involves extrusion through an asymmetric ceramic filter. The method is detailed in co-owned U.S. patent application for Liposome Extrusion Method, Ser. No. 829,710, filed Feb. 13, 1986 now U.S. Pat. No. 4,737,323.

The liposomes may be further treated to remove unencapsulated drugs and/or other solute material. Conventional separation techniques, such as centrifugation, diafiltration, and molecular-sieve chromatography are suitable. The separation step should be carried out after sizing, since the sizing procedure itself can lead to liposome rupture and release of encapsulated drug. It will be appreciated that free drug removal will be necessary to remove the water-soluble, liposome-impermeable B-agonist drug from the liposome dispersion.

C. Liposome Concentrate

As indicated above, the liposome composition preferably contains the $\beta_2$-agonist drug predominantly in liposome-encapsulated form, i.e, in a form in which more than half, and preferably about 70% or more of the total drug is present in liposome encapsulated or liposome-entrapped form. One composition which contains predominantly encapsulated $\beta_2$-agonist is a liposome paste in which the encapsulated volume of aqueous medium is greater than about 50% and preferably about 70–75% of the total suspension volume, reflecting the approximate percentage of liposome encapsulated drug.

In a preferred method of forming the paste, a relatively dilute liposome dispersion, prepared as above, is concentrated by ultrafiltration, and more preferably, tangential-flow ultrafiltration. Briefly, the dispersion is recycled continuously through a frame-and-plate type filtration device having one or more filtration units, each composed of a central filtrate screen and a pair of filters supported on the upper and lower sides of screen. The dispersion is pumped under pressure across both membranes, and aqueous medium is drawn though the filters across a pressure gradient of typically about 5–25 psi, with higher gradients being required as the recycled material becomes more concentrated. The material is recycled through the system until a desired liposome concentration, which can be as high as 70–75% liposomes, expressed in percentage of liposome-encapsulated volume, is achieved. The ultrafiltration membranes used in the device may be conventional membranes, such as polysulfone, nylon, or cellulose acetate membranes which have a size cutoff of between about 10,000–100,000 daltons.

Other concentration methods, such as drying and centrifugation to pellet liposomes, may also be used to form the liposome concentrate of the invention, although ultrafiltration is preferred, because of advantages of sterility, large-volume capacity, and relatively mild conditions to which the liposomes are exposed.

D. Liposome/Propellant Composition

A second preferred liposome composition, according to the invention, is a suspension of dried liposomes particles in a propellant solvent. The liposomes particles are formed preferably by spray drying a dilute aqueous suspension of liposomes, according to conventional procedures. Briefly, the liposome suspension which is spray dried is preferably a 3–6% by weight suspension of liposomes containing a predominance of partially or totally hydrogenated lipid components, such as PC, whose phase transition temperature is above the drying temperature to be used in the drier, typically between about 40°–45° C. The drying apparatus is itself a conventional spray dry machine, such as a Buchi 190 Mini Spray Dryer. The liposome suspension is pumped through an atomizer in spray form and dried by a stream of heated air or nitrogen which carries the liposomes into a spiral collection chamber. Exemplary temperature conditions are: 41° C. for the initial liposome suspension temperature and drying gas stream, and 31° C. for the collection chamber.

The propellant solvent is one in which (a) liposomes can be suspended without damaging the lipid integrity of the particles, and (b) the drug has a relatively low partition coefficient with respect to water, such that the bulk of the drug remains associated with the liposomes. Example V below examines the stability of liposome emulsions in six fluorocarbon propellants. The propellants which were tested are "Freon 11" ($CCl_3F$), "Freon 12" ($CCl_2F_2$), "Freon 22" ($CHClF_2$), "Freon 113" ($CCl_2FCClF_2$), "Freon 114" ($CClF_2CClF_2$), and "Freon 115" ($CClF_2CF_3$). Three different formulations of liposomes were tested, and all showed good stability in Freon 113, 114, and 115. Best stability was achieved with liposomes containing saturated acyl-chain-phospholipids. It is noted here that Freon 114 and 115 can be mixed in proportions which give a proper vapor pressure at room temperature for an aerosol canister.

To form the desired composition, the spray-dried liposomes are added to the selected propellant or propellant mixture, to a final liposome concentration of about 1 to 20 percent by weight propellant. The liposomes/propellant suspension is packaged in a conventional cannister equipped with a metering valve, as described below.

II. Aerosolizing Liposomes

This section describes exemplary devices useful in delivering liposome compositions of the type described above in nebulized or atomized, metered-dose form. These devices are discussed below in relation to the three general types of liposome suspensions to be nebulized.

A. Dilute Liposome Suspensions

Pneumatic nebulizers which are designed for atomizing aqueous sample are commercially available, and operate according to well-known procedures, such as those outlined in Example IV. Typically, the nebulizing operation is carried out at a pressure of about 5–15 psi, and the aqueous particles formed are typically in the range of about 2–6 microns. The device may be controlled to produce a measured quantity of aerosolized liposomes, according to known operational variables (reference 4).

Because the aerosolization procedure may result in mechanical disruption of a liposome suspension, it may be important to establish that the nebulizing process does not significantly affect liposome integrity and size. The effect of aerosolization by a pneumatic nebulizer on liposome particle size and loss of encapsulated material is reported in Example IV. Here four liposome compositions having in vitro drug efflux half lives ranging from 206 minutes to 5256 minutes, and each having an original particle size distribution between about 0.180–0.300 microns, were examined for size change and loss of encapsulated material after aerosolization at 5 psi. As reported in Table 7 of Example IV, no change in liposome size or loss of encapsulated material was observed for three of the preparations, and only a slight loss of encapsulated material and moderate increase in size was observed for liposomes with the lowest drug efflux half life.

Another device suitable for aerosolizing an aqueous suspension of liposomes, and preferably a relatively dilute suspension containing less than about 25%–30% encapsulated aqueous volume, uses ultrasonic energy to break up a carrier fluid into a fine mist of aqueous particles. The ultrasonic nebulizer device has been found to produce a liposome aerosol mist whose particle sizes are about the same as those formed by a compressed air nebulizer, i.e., between about 2–6 microns. The effect on liposome size and retention of encapsulated material by ultrasonic aerosolization was examined in a study similar to the one just described, and also reported in Example IV below. The results of that study, summarized in Table 8 in Example IV, are consistent with the earlier study, showing that the aerosolizing process has substantially no effect on liposome size or release of encapsulated material, except a relatively minor effect on the liposomes composed predominantly of short, unsaturated acyl chain lipids.

B. Liposome Paste Suspensions

For aerosolizing a liposome paste of the type used for delivery of a water-soluble, liposome-permeable drug, the paste is first mixed with a carrier solvent, to form a diluted dispersion which can be aerosolized. The carrier solvent may be an aqueous medium, in which case the paste is diluted to a form suitable for spraying, such as by a pneumatic or ultrasonic nebulizer. The amount of diluent added is sufficient to dilute the paste to a sprayable dispersion, preferably containing less than about 30% total encapsulated volume. Assuming the paste has an initial encapsulated volume of 70–75% of the total paste volume, it can be appreciated that a given volume of the paste must be diluted with at least one and two volumes of diluent.

A suitable aerosolizing device for the making and spraying the emulsion includes (1) separate chambers for holding the paste and carrier vehicle liquids, (2) a mixing chamber where metered amounts of the two liquids are mixed, and (3) means for aerosolizing the contents of the mixing chamber. Dispensing devices designed for storing two different liquids in isolation from each other, and for intermittent dispensing of the liquids in contact with each other are known, as disclosed, for example, in U.S. Pat. No. 3,325,056. Where the device operates to mix the paste with an aqueous carrier medium, the pneumatic or ultrasonic energy used to produce aerosolization can also be used to effect rapid and complete mixing of the two fluids. The releasing means includes a valve structure communicating with the mixing chamber, to allow release of the contents of the mixing chamber through a nozzle. Here it is noted that the mixing and spraying steps are carried out in relatively quick succession, before appreciable leakage of encapsulated drug into the aqueous carrier vehicle can occur, i.e., while the drug is still predominantly in liposome-encapsulated form.

C. Preformed Liposome/Propellant Suspensions

Valved container devices for aerosolizing particulate material suspended in a propellant solvent are well known. These devices generally operate by supplying a particle suspension to a metering chamber, and forcing the contents of the chamber through a nozzle under pressure, to aerosolize a metered quantity of the suspension. In the present invention, the particle/propellant suspension is preferably a suspension of spray-dried lipids in a propellant solvent, formed as in Section ID. The suspension is bottled and stored in a pressurized cannister in the device, in a conventional manner. The concentration of liposomes in the pressurized suspension is as to supply, in each metered dose, a therapeutic dose of the $\beta_2$-agonist drug.

III. Therapeutic Applications $\beta_2$-adrenoreceptor agonists are used as bronchodilators in the treatment of bronchial asthma, emphysema, bronchitis, and bronchiectasis, and also in the treatment of peripheral vascular disease and shock, and may also be used to delay delivery in cases of premature labor.

Figure 1B:
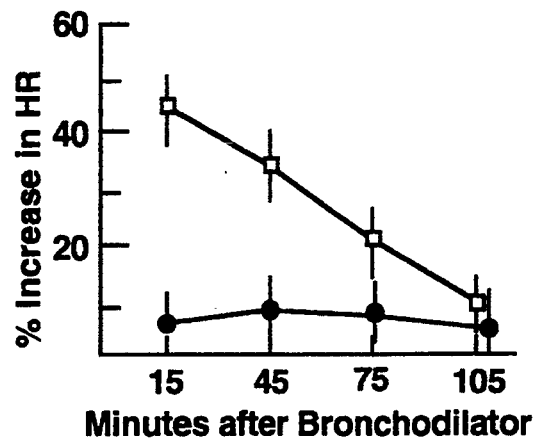

One undesired side effect of $\beta_2$-agonists, as noted above, is short term tachycardia, resulting from uptake of the drug from the respiratory tract into the bloodstream. Earlier studies reported in the above-mentioned co-pending patent applications for "Inhalation Method and System", have demonstrated that drug delivery in liposomal form eliminates or significantly reduces the high, initial increase in heart rate seen when $\beta_2$-agonist drugs, such as MPS, are administered to the lung in free form, This liposome-protective effect is illustrated in FIGS. 1A and 1B, which graph percent increases in heart rate, above a pre-drug level, in animals receiving a $\beta_2$-agonist in free (open squares), or liposomal form. The two liposomal formulations are characterized by relatively short drug-release half life (open circles, FIG. 1A), or a relatively long drug-release half life (closed circles, FIG. 1B). Heart rate was measured at 15, 45, 75, and 105 minutes after drug administration, and immediately before the animal received a bronchoconstricting dose of histamine by inhalation. As seen, free drug produced a relatively high initial heart rate increase, with a slow decline over the test period. With liposome-encapsulated drug, however, the increase in heart rate was substantially lower and more constant over the test period. It is also evident from a comparison of the liposome-drug data in FIGS. 1A and 1B that the extent of systemic drug effects can be modulated significantly according to drug-release characteristics of the liposomes.

Figure 2:
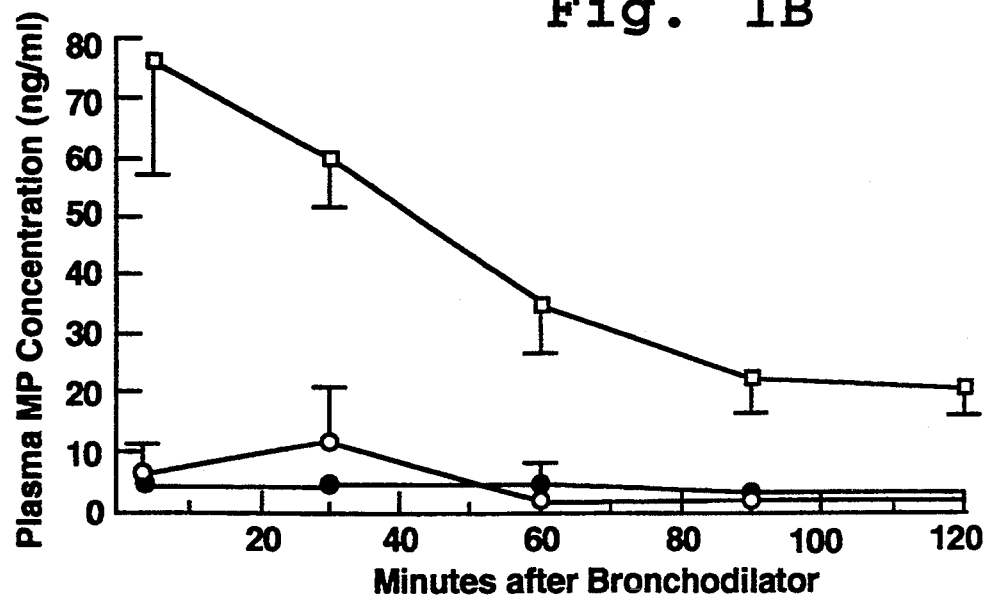
FIG. 2 shows plasma concentrations of MPS in test subjects following administration of free drug (open squares) and drug encapsulated in each of the FIG. 1 liposome formulations.

The reduction in tachycardia is consistent with blood plasma drug levels measured during the same test period, as seen in FIG. 2. In animals receiving free-drug, blood levels rose to nearly 80 ng/ml within 15 minutes of drug administration, then fell slowly over a two-hour period to about 20 ng/ml. By contrast, blood levels of MPS in animals receiving the drug in liposomal form reached a high of about 12 ng/ml in the less stable liposomes, and about 7 ng/ml in the more stable liposomes.

Figure 3:
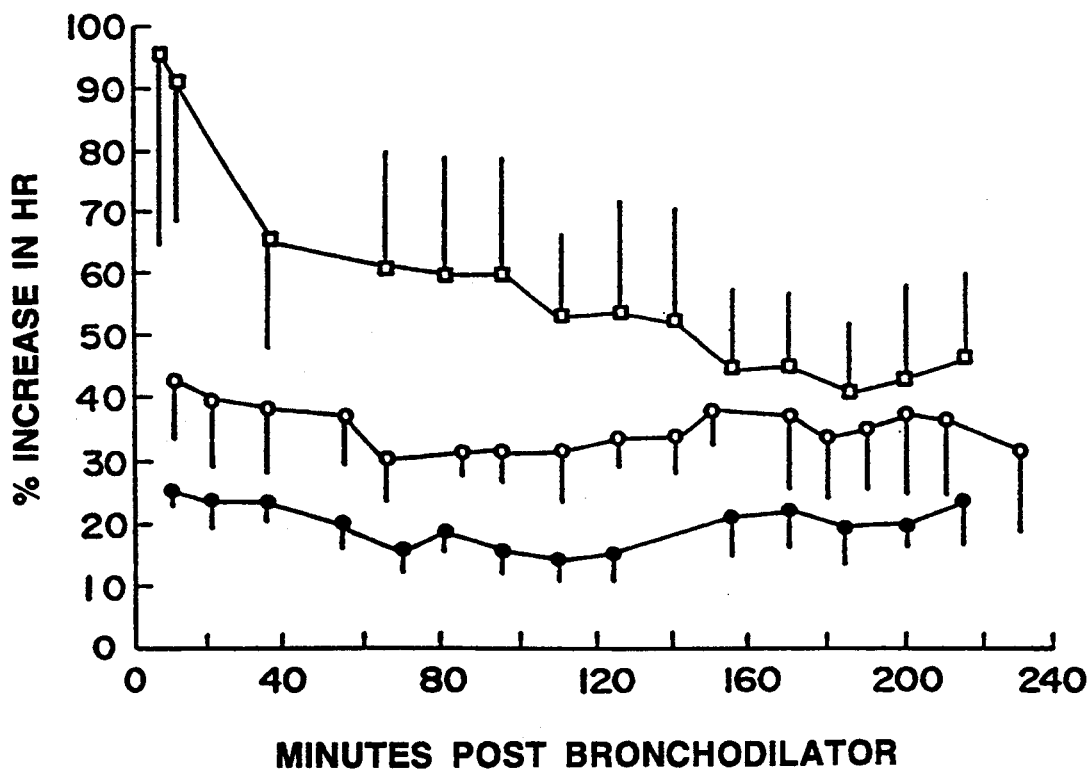
FIG. 3 is a plot showing percent increase in heart rate in test subjects following administration by inhalation of free metaproteranol sulfate (MPS)(open squares) or MPS-encapsulated in liposomes having relatively long (closed circles) or relatively short (open circles) in vitro drug efflux rates.

A second study, which examined both the increase in heart rate and drug protection against bronchoconstriction (increase in airway resistance), over an extended drug-response time, is detailed in Example VI. The data on increased heart rate in response to a single administration of drug in free or liposomal form are seen in FIG. 3, where the symbols in the figure represent the same free-drug or liposomal drug formulations as in FIGS. 1 and 2. The data support the findings of the earlier study: that liposomes significantly reduce systemic side effects, and the degree of reduction can be controlled within limits by the lipid composition of the liposomes.

Figure 4:
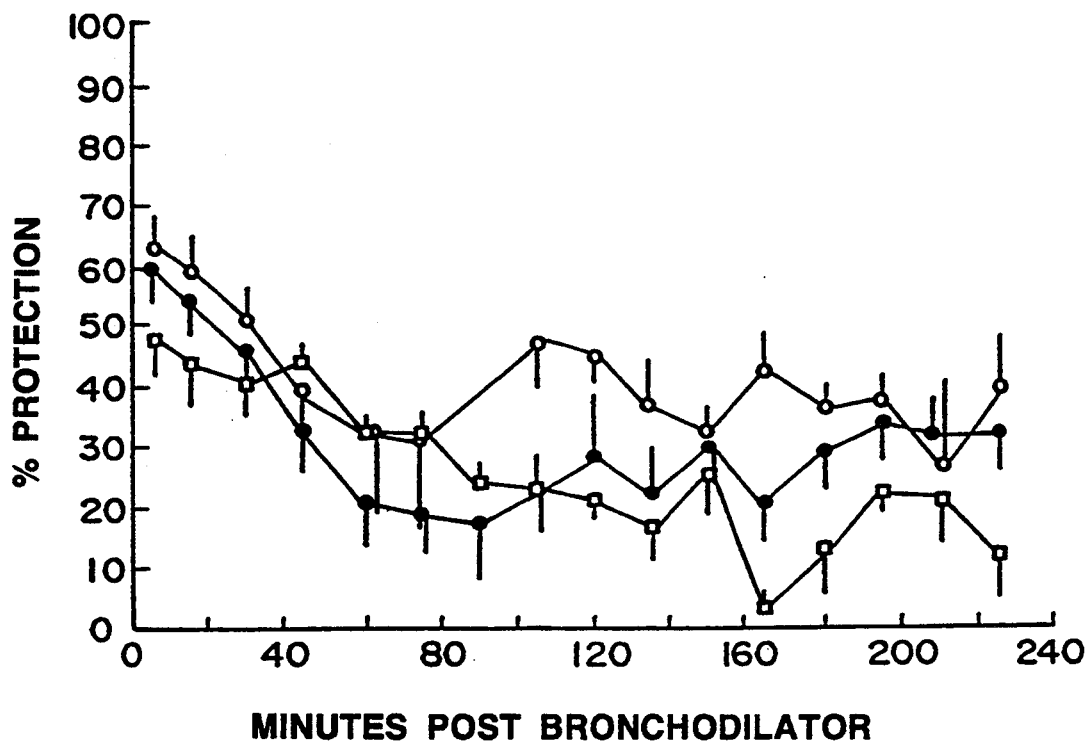
FIG. 4 is a plot showing percent protection against acetylcholine-induced bronchoconstriction in test subjects following administration of MPS, as in FIG. 3.

FIG. 4 shows the degree of protection against bronchoconstriction provided by the various free and liposomal formulations. This parameter reflects the increase in airway resistance (bronchoconstriction) immediately after administration of acetylcholine to induce bronchoconstriction. That is, the percent protection indicates the percent increase in airway resistance relative to a pre-drug level, following acetylcholine. As seen from FIG. 4, the degree of protection provided by drug encapsulated in either of two different liposome formulations was substantially the same as for free drug, over an approximately four-hour test period. It is noted that this study involved relatively high dose levels of MPS (which were needed to protect against the severe bronchoconstriction induced by the acetylcholine aerosols).

Summarizing the results of the earlier studies, administration of a $\beta_2$-agonist drug in liposomal form to the respiratory tract significantly reduces side effects related to systemic drug uptake, and at high drug concentrations, gives substantially the same degree of protection against bronchoconstriction over a several-hour period, as the free drug.

It has now been discovered, in studies reported herein, that $\beta_2$-agonist drugs, when administered at a therapeutic dose in liposome aerosol form, provide significantly greater bronchodilation at extended times after drug administration (greater than about 1 hour after drug administration) than does the same amount of drug administered in free form. The study described in Example VII illustrates the increased protection, at extended time periods, achievable with liposomal drug administration. Briefly summarizing the Example VII study, terbutaline sulfate or salbutamol sulfate, in either free or liposomal form, was administered by inhalation. At several times after drug administration, the test animal was challenged with aerosolized histamine, to induce bronchoconstriction. At the beginning of each test, prior to administration of the $\beta_2$-agonist, and immediately after each histamine dose, airway resistance and lung compliance in the animal were measured. Airway resistance, which is measured at points of equal lung volume during the breathing cycle, provides a measure of the resistance to gas flow through the large air passages of the lung. Lung compliance, which is measured at zero flow points in the breathing cycle, reflects the pressure changes required to effect the lung volume change over the breathing cycle. The resistance and compliance values determined at the beginning of the test serve as baseline values for determining the percentage changes in resistance and compliance, in response to histamine-induced bronchoconstriction.

The therapeutic doses of terbutaline sulfate, and salbutamol sulfate which were used in the present study were determined as follows. Recommended human doses, based on drug/body weight, as suggested by the drug supplier, were assumed to be approximately the minimum doses which produce maximal or near-maximal short-term protection against bronchoconstriction. These drug doses, adjusted for the body weight of the test animal, were administered by inhalation in free form, and their effects on the histamine-induced bronchoconstriction were determined as above. MPS was also tested in the initial drug-dose study. Of the three drugs tested, salbutamol provided good protection against bronchoconstriction at the recommended dose. For both MPS and terbutaline, it was necessary to double the recommended dose in order to achieve effective protection. The therapeutic doses per animal determined from the the study were: 39 $\mu g$ MPS ($2\times$ recommended dose); 15 $\mu g$ terbutaline ($2\times$ recommended dose); and 1.5 $\mu g$ salbutamol ($1\times$ recommended dose). The therapeutic dose of MPS is approximately 60 times less than the dose used in the experiments reported above, and in Example VI.

FIG. 5A shows changes in airway resistance measured in animals treated with a therapeutic dose of either free (open squares) or liposome-entrapped (crosses) terbutaline sulfate. The liposomes employed in the study have the same composition as the Preparation-2 liposomes employed in the study above, i.e., have a drug release half life of about 250 minutes in vitro. Each time point was calculated as the difference in airway resistance shortly after histamine administration and at the beginning of the test (baseline value) divided by the baseline value. Thus the initial resistance values of 60% in the figure indicate a 60% increase in airway resistance with respect to baseline. Both free and liposomal drug formulations provide about the same degree of initial protection against bronchoconstriction. However, whereas airway resistance increased to about 95% with the liposomal form of the drug, at the end of the 115 minutes test period, it increased to over 160% in the same period with free drug administration. Thus, the liposomal form of the drug provides substantially greater protection against bronchoconstriction, at times greater than 1 hour after drug administration, than the same therapeutic dose free drug.

Figure 5A:
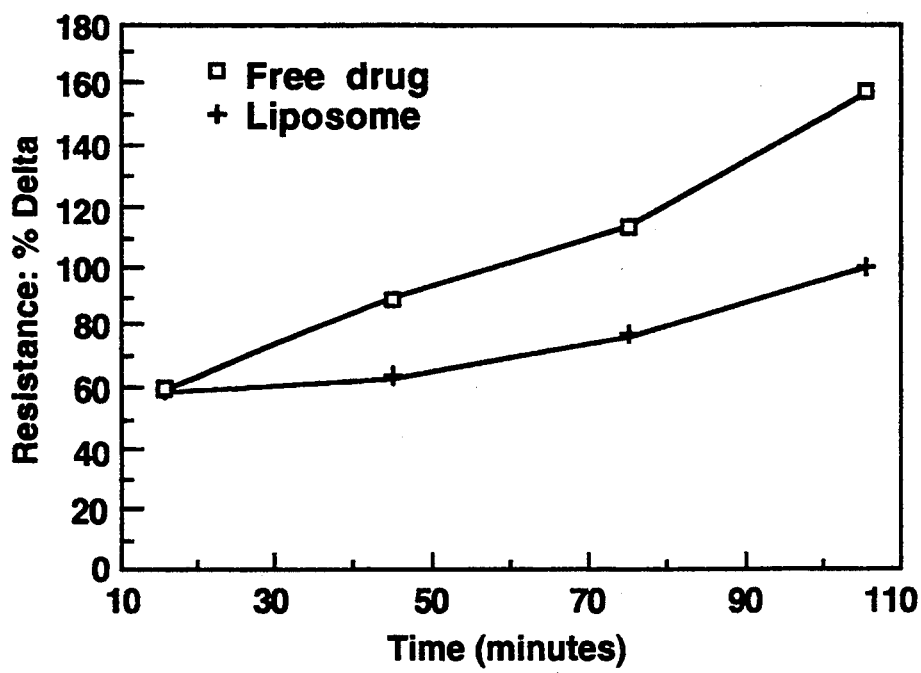
FIGS. 5A and 5B show changes in airway resistance (5A) and lung compliance (5B) caused by broncho-provocation with aerosol histamine solutions after administration of terbutaline sulfate, via the respiratory tract, in free (open squares) and liposomal (crosses) form.
Figure 5B:
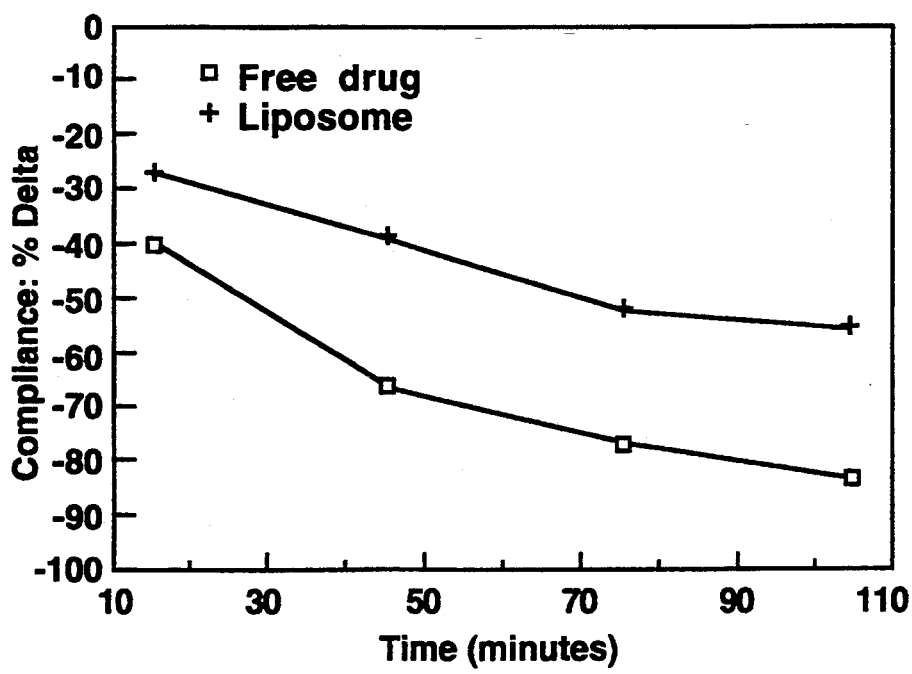

FIG. 5B shows changes in lung compliance under the same test conditions. At all time points at which bronchoconstriction was induced, the lung compliance after histamine-induced bronchoconstriction was substantially greater than that in animals receiving the drug in free form.

Figure 6A:
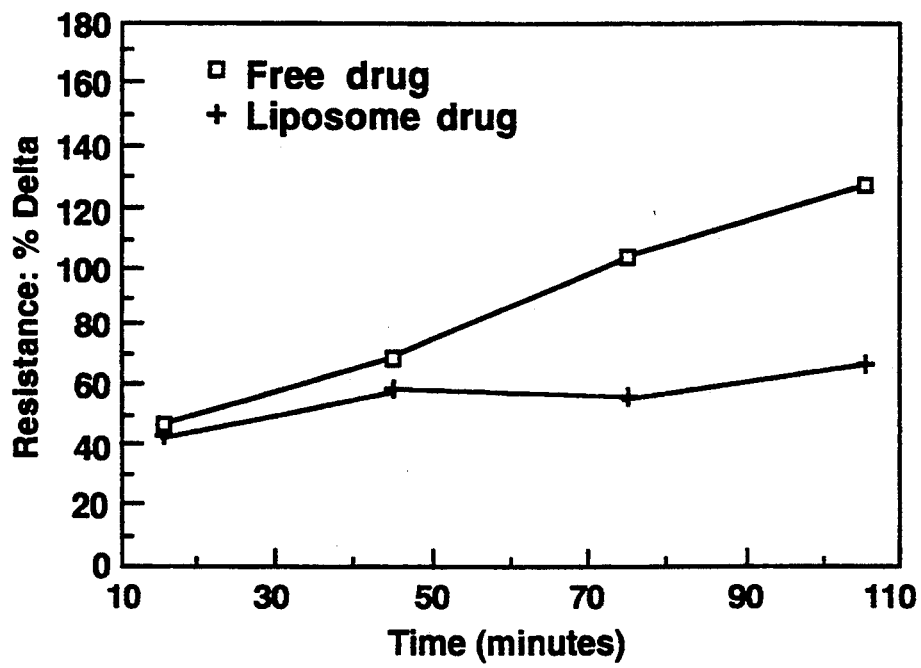
FIGS. 6A and 6B show changes in airway resistance (6A) and lung compliance (6B) caused by broncho-provocation with aerosol histamine solutions after administration of salbutamol sulfate, via the respiratory tract, in free (open squares) and liposomal (crosses) form.
Figure 6B:
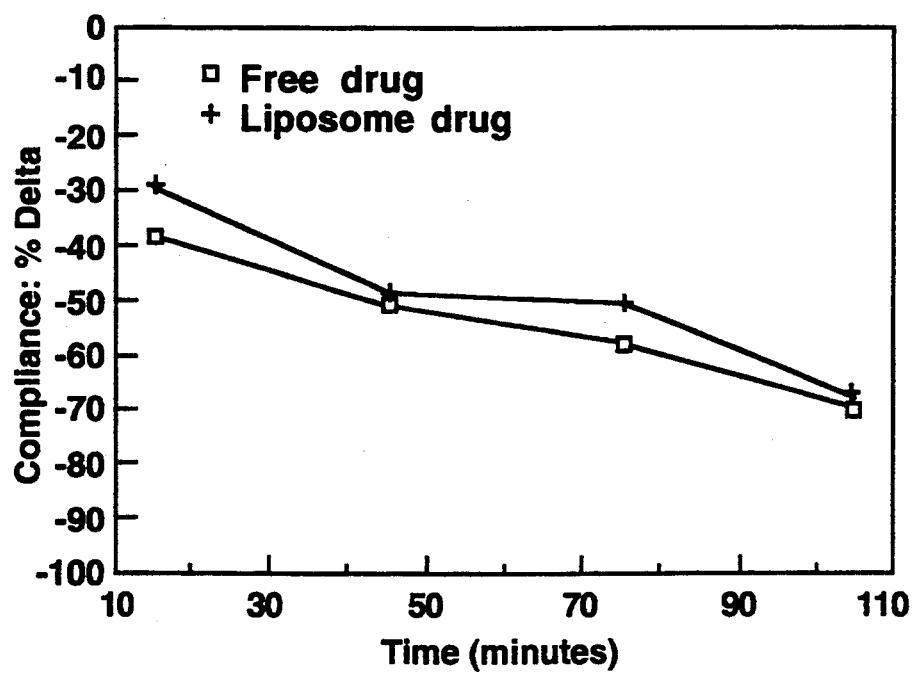

A similar study was conducted with salbutamol sulfate, which was administered at a therapeutic dose in either free (open squares) or liposome-encapsulated (crosses) form. The data plotting changes in airway resistance and lung compliance as a function of time after drug administration are shown in FIGS. 6A and 6B. The data are consistent with the results seen with terbutaline, showing that the liposomal form of the drug provides substantially greater protection against bronchoconstriction, at times after about 1 hour, than does the free drug.

From the foregoing, it can be appreciated that the method and system of the invention provide several advantages over free drug administration of $\beta_2$-agonists, for treatment of bronchoconstriction. First, undesired side effects due to rapid uptake of free drug from the lungs are largely avoided. Therefore, increased heart rate, dizziness, insomnia and other symptoms frequently complained of are eliminated or minimized. Further, even at doses which are minimal for effective free-drug bronchodilation, administration of the drug in liposomal form gives initial protection against bronchoconstriction which is comparable to that of the free drug.

The greater protection against bronchial constriction seen more than about an hour after drug administration has two obvious benefits. First, the patient receives longer periods of relief with each dosing, and therefore the intervals between dosing can be extended, and greater patient compliance can be achieved. Secondly, in terms of long-term patient health, the stress of frequent and transient side effects are reduced.

The liposomes may also serve as a vehicle of codelivery of other drugs or protective agents. Further, the liposomes protect the respiratory tract from potential irritation that can be caused by inhalation of micronized drug particles sprayed from a propellant solvent.

The following examples illustrate various compositional parameters, methods of preparation and use, and pharmacokinetic characteristic of $\beta_2$-agonist/liposome compositions of the present invention. The example are intended to illustrate, but not limit, the scope of the invention.

EXAMPLE I

Effect of Lipid Chain Length and Saturation on Drug Efflux

Metaproteranol sulfate (MPS) was obtained from Vinchem Inc. (Chatham, N.J.); $\alpha$-tocopherol ($\alpha$-T), from Sigma Chemical Co. (St. Louis, Mo.); and $^{14}$-C sucrose, from Amersham Co. (Arlington Hts, Ill.). Egg phosphatidyl choline (EPC), soy phosphatidyl choline (SPC), hydrogenated egg phosphatidyl choline (HEPC), hydrogenated soy phosphatidyl choline (HSPC), dioleoyl phosphatidyl choline (DOPC), dimyristoyl phosphatidyl choline (DMPC), dipalmitoyl phosphatidyl choline (DPPC), and distearoyl phosphatidyl choline (DSPC), were obtained from Avanti Polar Lipids (Birmingham, Ala.). The 8 PC lipids have the transition temperatures ($T_c$) and fatty acyl chain compositions given in Table 1 below, where the lipids having greater acyl chain lengths and/or degrees of saturation are arranged in descending order.

TABLE 1

| PC | $T_c$(C.°) | Fatty Acyl Composition |
|---|---|---|
| SPC | −15 to −7 | 16:0(12%) 18:2(73%) |
| DOPC | −22 | 18:1 |
| EPC | −15 to −7 | 16:0(42%) 18:1(28%) 18:2(16%) |
| DMPC | 23 | 14:0 |
| DPPC | 41 | 16:0 |
| HEPC | 55 to 65 | 16:0(36%) 18:0(60%) |
| HSPC | 55 to 65 | 16:0(13%) 18:0(87%) |
| DSPC | 55 | 18:0 |

For each of the 8 PC lipids, multilamellar vesicles (MLVs) were prepared by dissolving 350 $\mu$mole of the selected PC lipid with 1 mole percent of $\alpha$-T in chloroform. The dissolved lipid was evaporated to dryness under vacuum in a round-bottom flask to form a lipid film on the flask walls. A 5 ml solution containing 20 mg/ml MPS and $1.1 \times 10^7$ cpm $^{14}$C-sucrose in phosphate-buffered saline (PBS), pH 7.2, 290 mOsm, was added to the flask to cover the film. At the end of a 2-hour hydration period, the liposomes (MLVs) which formed were extruded successively two times each through a 0.4 and 0.2 micron uniform pore-size polycarbonate filter (Bio-Rad; Richmond, Calif.). Unencapsulated MPS and sucrose were removed by passage of the extruded MLVs through a Sephadex G-75 gel-exclusion column. The percent encapsulation of MPS ranged from a low of about 0% for DMPC MLVs to a high of 21% for DPPC MLVs (Table 2). Encapsulation of $^{14}$C-sucrose ranged from a low of 0.2% for DMPC MLVs to a high of 18% for the DPPC MLVs.

To measure leakage of encapsulated solutes from the MLV preparations, each preparation was incubated at 37° C. for a period of up to 42 hours. Timed aliquots taken periodically during the 42-hour incubation period were passed through a gel-exclusion column, and the lipid, MPS, and sucrose present in the liposome peak were assayed by conventional methods. The loss of lipid-associated drug during the course of the incubation was used to determine the drug efflux half life ($t_{\frac{1}{2}}$) for each preparation, calculated as the time required for the drug/lipid ratio to fall by one-half. The calculated efflux half lives, expressed in minutes, are shown in Table 2 below.

TABLE 2

| | Encapsulation | |
|---|---|---|
| PC/$\alpha$-T (10:0.1) | % MPS Encapsulated | $t_{\frac{1}{2}}$ MPS (minutes) |
| SPC | 6 | 22 |
| DOPC | 4 | 41 |
| EPC | 10 | 48 |
| DMPC | 0 | — |
| DPPC | 21 | 574 |
| HEPC | 5 | 6426 |
| HSPC | 8 | 2175 |
| DSPC | 13 | 6366 |

As seen from data in Table 2, the rate of efflux of drugs from the MLVs can be selectively increased from a half life of about 22 minutes to one showing no appreciable leakage over a 42-hour period, by increasing the length and degree of saturation of the acyl chains in the phospholipids making up the liposomes. A comparison of the half-life data in Table 2 with the transition temperature data in Table 1 shows that each of the MLV preparations having a relatively high efflux half life (greater than 500 minutes) is composed of a PC whose transition temperature is above the temperature at which the liposomes were incubated. No appreciable loss of the relatively impermeable $^{14}$C-sucrose from the liposomes was detected over the 42 hour incubation period, indicating that the observed drug efflux is not due to liposome breakdown.

EXAMPLE II

Effect of Charged Lipids on Drug Efflux

Egg phosphatidyl glycerol (EPG), dioleoyl phosphatidyl glycerol (DOPC), and distearoyl phosphatidyl choline (DSPC) were obtained from Avanti Polar Lipids (Birmingham, Ala.).

Liposomes (MLVs) containing the lipid composition indicated at the left in Table 3 below, were prepared substantially as described in Example I, starting with initial concentrations of 312 μmole of the selected PC, 35 μmole of the selected PG, and 3.5 μmole α-T. For each lipid composition, the dried film was hydrated in 5 ml of the MPS/sucrose solution described in Example I, and the liposomes were sized by extrusion through polycarbonate filters and separated from non-encapsulated material by molecular-sieve chromatography, as above. The percentages of encapsulated MPS are shown in the middle column in Table 3. A comparison of the encapsulation data from Tables 2 and 3 shows that the presence of 10% PG generally increased drug encapsulation efficiencies. This effect was also observed for $^{14}$C-sucrose encapsulation.

The eight MLV fractions were each incubated at 37° C. for 42 hours, and the drug efflux half lives determined from the measured loss of drug at several intervals over the 42-hour incubation period. The calculated efflux rate half lives are shown at the right in Table 3.

TABLE 3

| PC/PG/α-T (9:1:0.1) | % MPS Encapsulated | $t_{\frac{1}{2}}$ (minutes) |
| --- | --- | --- |
| SPC/EPG | 14 | 92 |
| DOPC/DOPG | 13 | 289 |
| EPC/EPG | 7 | 151 |
| DPPC/EPG | 16 | 110 |
| DPPC/DPPG | 23 | 5256 |
| HEPC/EPG | 15 | 526 |
| HSPC/EPG | 14 | 856 |
| DSPC/DSPG | 20 | 14100 |

The addition of 10 mole percent PG to the liposome/lipid mixture had one of two effects relative to PCs alone (Example I). For the shorter, more unsaturated PC acyl chains, an increase in half life for MPS leakage was seen as a result of the negative charge imparted to the bilayer by PG. With the saturated, longer chain length lipids, the more important factor seems to be the degree of acyl chain unsaturation of the added PG—for example, in the case of EPG, decreasing the overall membrane saturation and thus decreasing measured half lives for MPS leakage. Where a PG derivative of the same saturation chain length as the PC was used (DPPG/DSPG), similar or longer half-lives than with PC alone resulted. As in Example I, no appreciable loss of $^{14}$C-sucrose was observed in any of the preparations.

EXAMPLE III

Effect of Cholesterol on Drug Efflux

Eight liposome MLV preparations containing one of the eight PCs shown at the left in Table 4, cholesterol (CH), and α-T in a molar ratio of 6:4:0.1, and containing encapsulated MPS and $^{14}$C-labeled sucrose, were prepared as in Example I. The MLV preparations, after extrusion through 0.4 and 0.2 polycarbonate membranes and treatment with molecular-sieve chromatography to remove unencapsulated material, gave the percent encapsulation of MPS indicated in the middle column in Table 4.

The eight MLV fractions were each incubated for a 42-hour period to determine drug efflux half lives in accordance with the methods described above. The calculated half lives are shown at the right in Table 4.

TABLE 4

| PC/CH/α-T (6:4:0.1) | % Encapsulated MPS | $t_{\frac{1}{2}}$ (minutes) |
| --- | --- | --- |
| SPC/CH | 8 | 103 |
| DOPC/CH | 9 | 313 |
| EPC/CH | 10 | 206 |
| DMPC/CH | 9 | 201 |
| DPPC/CH | 11 | 146 |
| HEPC/CH | 11 | 220 |
| HSPC/CH | 10 | 330 |
| DSPC/CH | 13 | 421 |

In the presence of 40 mole percent cholesterol, drug efflux half lives associated with unsaturated, shorter-chain lipids were longer than those obtained for PC alone. For the more saturated, longer chain-length lipids, 40 mole percent cholesterol decreased half lives significantly over that observed for PC alone.

The effect of cholesterol and PG was examined in a similar type of study using MLVs composed of 50 mole percent of a selected PC, 10 mole percent of a selected PG, 40 mole percent of cholesterol, and 0.1 mole percent α-T, as indicated at the left in Table 5. The drug encapsulation data for the eight MLV preparations and the corresponding drug efflux half lives are shown at the middle and right columns, respectively, in Table 5. As seen, the presence of 10 mole percent PG significantly increased the drug efflux half lives of each PC lipid with respect to the Table 4 lipid composition containing PC and cholesterol only.

TABLE 5

| PC/PG/CH/α-T (5:1:1:0.1) | % Encapsulated MPS | $t_{\frac{1}{2}}$ (minutes) |
| --- | --- | --- |
| SPC/EPG/CH | 10 | 326 |
| DOPC/DOPG/CH | 11 | 235 |
| EPC/EPG/CH | 12 | 250 |
| DMPC/DMPG/CH | 10 | 591 |
| DPPC/DPPG/CH | 12 | 941 |
| HEPC/EPG/CH | 13 | 334 |
| HSPC/EPG/CH | 12 | 553 |
| DSPC/DSPG/CH | 27 | 1148 |

Finally, eight liposome preparations containing one of the PC lipids indicated at the left in Table 6 (60 mole percent); cholesterol hemisuccinate, a negatively charged sterol (40 mole percent); and 0.1 mole percent α-T were prepared as above. CHHS was obtained from Sigma Chem Co. (St. Louis, Mo.). The eight preparations gave the encapsulation efficiencies and drug efflux half lives indicated in the middle and right columns, respectively, in Table 6 below. As seen, the presence of 40 mole percent cholesterol hemisuccinate gave uniformly high encapsulation efficiencies. The half lives are generally somewhat greater than those observed with the corresponding liposome preparations involving 40 mole percent cholesterol (Table 4 above), but significantly less than the corresponding lipid preparations containing 40 mole percent cholesterol plus 10 mole percent PG.

TABLE 6

| PC/CHHS/α-T (9:1:0.1) | % Encapsulated MPS | $t_{\frac{1}{2}}$ (minutes) |
|---|---|---|
| SPC/CHHS | 19 | 73 |
| DOPC/CHHS | 19 | 123 |
| EPC/CHHS | 24 | 77 |
| DMPC/CHHS | 20 | 129 |
| DPPC/CHHS | 18 | 245 |
| HEPC/CHHS | 20 | 601 |
| HSPC/CHHS | 19 | 856 |
| DSPC/CHHS | 23 | 768 |

EXAMPLE IV

Aerosolizing Aqueous Liposome Suspensions

This section examines the effect on liposome integrity, as judged by loss of encapsulated material and change in liposome size, of aerosolizing an aqueous liposome suspension.

Four liposome preparations were tested. Preparation #1 had a composition EPC/CH/α-T, at a molar ratio of 6:4:0.1; preparation #2, a composition of DSPC/CH/α-T, at a molar ratio of 6:4:0.1; preparation #3, a composition of DPPC/DPPG/CH/α-T, at a molar ratio of 5:1:4:0.1; and preparation #4, a composition of DPPC/DPPG/α-T, at a molar ratio of 9:1:0.1. The four preparation represent a wide range of drug-efflux half lives, measured as in Examples I–III above, as indicated in Table 7 below. The liposomes were prepared substantially as described in Example I, except that the aqueous solution used in preparing the liposomes contained carboxyfluorescein (129 mM) rather than MPS and $^{14}C$-labeled sucrose. Each of the four liposome preparations was extruded two times each through a 0.4 and 0.2 micron polycarbonate membrane to produce substantially homogeneous particle sizes in the particle size ranges indicated below in Tables 7 and 8 after the liposome suspensions were separated from unencapsulated material by extensive dialysis. The final concentration of liposomes in the aqueous suspension was 70 μmole total lipid per ml PBS.

For each lipid preparation, liposome size distribution and percent encapsulation was measured before aerosolization (B), after aerosolization (A), and in the suspension which remained in the nebulizer (R). The sizes of liposomes in the suspension were determined by using a Nicomp Instruments Laser Particle Sizer Model 200 (Hyak-Royco, Menlo Park, Calif.). The machine was calibrated periodically with monodisperse latex beads supplied by the manufacturer for use as external standards.

The percent encapsulated carboxyfluorescein was determined according to standard procedures.

The size and percent encapsulation data for liposome preparations before and after aerosolization by the pneumatic nebulizer are shown in Table 7 below. The device used was a De Vilbiss No. 646 Pneumatic Nebulizer (Somerset, Pa.), operated at 15 psi. As seen from the data, aerosolization of the liposomes resulted in only a small loss of encapsulated material, ranging from about 8% for the liposome preparation having the lowest efflux half life to about 1% for the material having the highest efflux half life. No significant change in the size distribution of liposomes was observed for any of the four liposome preparations after aerosolization.

TABLE 7

| Preparation | | % Encap. ± s.d.(n = 3) | Median Lip. size (nm) |
|---|---|---|---|
| 1 | B | 96.2 ± 0.11 | 214, 210–218 |
| $t_{\frac{1}{2}}$ = | A | 88.5 ± 0.13 | 375, 315–428 |
| 206 min. | R | 95.9 ± 0.04 | 193, 189–200 |
| 2 | B | 95.5 ± 0.20 | 230, 214–268 |
| $t_{\frac{1}{2}}$ = | A | 93.0 ± 0.08 | 200, 180–240 |
| 421 min. | R | 96.7 ± 0.13 | 200, 190–218 |
| 3 | B | 97.2 ± 0.63 | 327, 271–450 |
| $t_{\frac{1}{2}}$ = | A | 93.4 ± 0.04 | 257, 225–327 |
| 941 min. | R | 96.2 ± 0.93 | 353, 300–400 |
| 4 | B | 96.1 ± 0.19 | 214, 193–231 |
| $t_{\frac{1}{2}}$ = | A | 95.1 ± 0.11 | 218, 171–266 |
| 5256 min. | R | 96.5 ± 0.02 | 225, 200–276 |

The effect on the integrity of the four liposome preparations of aerosolization by an ultrasonic nebulizer was also examined. The nebulizer used was a DeVilbiss Pulmosonic Model 25 Ultrasonic Nebulizer (Somerset, Pa.), operated at a powder mode of 3 kHz. The percent carboxyfluorescein encapsulation and size distribution, measured as above, are shown in Table 8 below for each of the four preparations, measured before (B) and after (A) aerosolization and for material remaining in the nebulizer (R). The results are substantially identical with the results obtained for the same preparations aerosolized by a compressed-air device.

TABLE 8

| Preparation | | % Encap. ± s.d.(n = 3) | Median Lip. size (nm) |
|---|---|---|---|
| 1 | B | 95.6 ± 0.10 | 316, 285–375 |
| | A | 89.4 ± 0.65 | 261, 250–279 |
| | R | 94.9 ± 0.45 | 207, 188–222 |
| 2 | B | 98.6 ± 0.08 | 240, 185–300 |
| | A | 96.8 ± 0.07 | 214, 200–240 |
| | R | 97.7 ± 0.53 | 163, 150–189 |
| 3 | B | 98.1 ± 0.09 | 257, 240–270 |
| | A | 96.0 ± 0.09 | 254, 244–270 |
| | R | 97.2 ± 0.10 | 240, 171–600 |
| 4 | B | 98.5 ± 0.02 | 333, 310–375 |
| | A | 96.2 ± 0.01 | 220, 204–231 |
| | R | 96.8 ± 0.03 | 220, 208–230 |

EXAMPLE V

Liposome Stability in Fluorocarbon Propellants

This section examines the stability of three liposome preparations in chlorofluorocarbon propellant solvents. The first liposome preparation, referred to as formulation 1, contained DPPC/DPPG/α-T at a molar ratio of 9:1:0.1; the second preparation, designated formulation 2, contained EPC/EPG/α-T at a molar ratio of 9:1:0.1; and the third preparation, designated formulation 3, was composed of EPC/EPG/CH/α-T at a molar ratio of 5:1:4:0.1. The liposomes were prepared substantially as described in Example I, except that aqueous solution used in forming the MLVs contained bovine serum albumin (BSA) and 1 μM carboxyfluorescein (CF). MLV preparations extruded twice through each of a 0.4 and a 0.2 micron polycarbonate membrane were pelleted by centrifugation to remove unencapsulated material, and resuspended in PBS to a final lipid concentration of about 20 μmol/ml. The six propellant solvents used are "Freon 11" ($CCl_3F$), "Freon 12" ($CCl_2F_2$), "Freon 22" ($CHClF_2$), "Freon 113" ($CCl_2FCClF_2$), "Freon 114" ($CClF_2CClF_2$), and "Freon 115" ($CClF_2CF$).

An aqueous suspension of each preparation in PBS (3 ml) was added to each of the 6 fluorocarbon solvents (10 ml) in a pressurized vial, and the vials were shaken on a mechanical shaker for 24 hours to maintain a water-and-oil emulsion. After the shaking period, the bulk liquid phases in each vial were allowed to reform by settling, and the upper aqueous phase was removed by aspiration. The liposomes in the aqueous phase were pelleted by centrifugation, and resuspended to the original lipid concentration in PBS. A portion of the resuspended liposomes was examined for particle size distribution, substantially as described in Example IV. A control sample, which was not exposed to a fluorocarbon but was otherwise handled identically to the other samples, showed a size distribution of between about 180 and 250 nm. The various samples which had been exposed to the six propellant solvents generally fell into two size ranges: those having sizes substantially identical to the control liposome sizes, i.e., between about 150 and 300 microns; and those having predominantly greater sized (400–500 microns or larger). The results, seen in Table 9 below, show that two of three preparations were stable in "Freon 12", that all three were stable in "Freon 114" and "Freon 115", and that MLVs containing largely saturated lipids (formulation 1) are generally more stable in fluorochlorocarbon propellants than those having predominantly unsaturated and/or shorter-chain phospholipids (formulations 2 and 3).

The pelleted and resuspended liposomes were also examined for release of BSA, representative of a relatively large molecular weight marker, and carboxyfluorescein, representative of a relatively small encapsulated marker. For each test, an aliquot of the resuspended liposomes were assayed by conventional methods for the appropriate marker. The marker concentrations are expressed in Table 9 in terms of amount marker per μmole of total lipid in the sample assayed (μg of BSA, μmole of CF). "ND" in the table means "not detectable".

TABLE 9

| Freon Propellant | Formulation 1 | | | Formulation 2 | | | Formulation 3 | | |
|---|---|---|---|---|---|---|---|---|---|
| | Size | BSA | CF | Size | BSA | CF | Size | BSA | CF |
| Control | 191 ± 26 | 14.3 | 11.4 | 248 ± 84 | 7.1 | 3.8 | 248 ± 60 | 8.2 | 5.9 |
| 11 | 171 ± 35 | 13.5 | 12.6 | 495 ± 293 | ND | ND | 560 ± 355 | ND | ND |
| 12 | 177 ± 44 | 11.4 | 10.3 | 231 ± 76 | 8.2 | 3.2 | 703 ± 400 | 4.0 | 1.9 |
| 22 | 1060 ± 570 | ND | ND | 475 ± 260 | 5.9 | 1.8 | 772 ± 430 | 12.0 | 1.1 |
| 113 | 157 ± 43 | 10.1 | 8.8 | 254 ± 60 | ND | ND | 160 ± 60 | ND | ND |
| 114 | 188 ± 40 | 11.2 | 9.3 | 236 ± 65 | 9.7 | 3.7 | 220 ± 50 | 7.8 | 8.0 |
| 115 | 181 ± 40 | 13.2 | 11.1 | 188 ± 50 | 8.6 | 3.2 | 240 ± 55 | 8.0 | 5.8 |

ND = not detectable

As seen from the data in the table, the loss of encapsulated material correlates generally with increased liposome size, both reflecting instability of liposomes in the particular fluorochlorocarbon solvent. However, both preparations 2 and 3 showed substantial loss of encapsulated material without significant size change when exposed to "Freon 113".

EXAMPLE VI

Treatment of Bronchoconstriction with High Dosages of MPS

This example examines the therapeutic effect of free and liposome-encapsulated metaproteranol sulfate (elevated dosage levels) on bronchoconstriction induced by aerosols of acetylcholine (ACH).

Two mongrel dogs, a 20 kg male and a 30 kg female, were anesthetized with an initial i.v. bolus injection of sodium thiopental (10 mg/kg body weight) and sodium pentabarbital (20 mg/kg body weight) and subsequent boluses of sodium thiopental every thirty minutes, or as needed, to maintain the dog in an anesthetized state over a four hour test period. The animals were intubated with a cuffed endotracheal tube, placed on a heat-exchange pad and artificially ventilated by a constant-volume respirator with room air at a frequency of 30 cycles/minute. An esophageal balloon catheter was introduced into the esophagus, connected to one port of a differential pressure transducer, and positioned in the mid-thorax to produce a maximal negative pressure inflection during inspiration. Air flow was monitored by a pneumotachograph connected to the endotracheal tube and the respirator and connected to a differential pressure transducer. Transpulmonary pressure was monitored by a differential pressure transducer, one port connected to a side arm of the tracheal tube and the other end connected to the esophageal balloon catheter. The flow and pressure signals were displayed continuously on an oscilloscope.

Liposome preparations having a lipid composition of DSPC/DSPG/CH/α-T at a molar ratio of 5:1:4:0.1 (Preparation 1) and EPC/EPG/CH/α-T at the same molar ratio (Preparation 2), each encapsulating metaproteranol sulfate at a final 2% drug concentration, were prepared as in Example III. As seen from Table 5 above, Preparation 1 has a drug efflux half life of about 1150 minutes, and Preparation 2, of about 250 minutes. Free MPS was administered as a 2% solution in PBS. Liquid aerosols of acetylcholine solutions sufficient to produce transient bronchoconstriction, as reflected by a 6–10 fold increase in total pulmonary resistance were administered via the endotracheal tube before, and at roughly 15 minute intervals following, aerosol administration of either free or liposome-encapsulated metaproteranol, each in doses corresponding to a total of about 2.4 rags MPS. All aerosols, including the acetylcholine aerosol, free-drug aerosol, and liposome aerosol, were generated with a pneumatic nebulizer (Bird #158, Somerset, Pa.), according to manufacturer's specifications, at 15 psi. Aerosol particle sizing performed with a Mercer Cascade Impactor (InTox Products, NM), indicated mass aerodynamic aerosol particle diameters within 2–6 microns.

The increase in heart rate monitored during the test period is plotted in FIG. 3 for the three drug formulations. The data show that liposomes effectively prevent rapid systemic uptake of the drug and stabilize systemic effects over a several-hour period following drug administration. Liposomes with a greater drug release half-life (solid circles) show a significantly lower heart rate increase than do less stable liposomes (open circles).

The effects of the free-drug and liposome aerosols on bronchoconstriction were measured approximately every fifteen minutes for four hours after initial drug administration. The experiment was repeated 3 times for each free and liposome-encapsulated drug formulation for each animal, and the values averaged. The results obtained for dog #1 are shown in FIG. 4, and are expressed in terms of percent protection from ACH-induced bronchoconstriction. Each point on the graph represents the mean ± standard error of the mean from results obtained in three experiments. As seen from the figure, free drug (open squares), Preparation 1 (closed circles), and Preparation 2 (open circles) all showed substantially the same degree of protection against ACH-induced bronchoconstriction.

EXAMPLE VII

Treatment of Bronchoconstriction with Therapeutic Dosages of Terbutaline, Salbutamol This example examines the therapeutic effect of free and liposome-encapsulated terbutaline sulfate and salbutamol (normal dosage levels) on histamine-induced bronchoconstriction in guinea pigs.

Male, Hartley guinea pigs, 320–450 gm, were anesthetized by IM injection of xylazine, ketamine, promazine (5:75:0.5 mg/kg animal weight). Respiratory airflow was measured with a whole body flow plethysmograph employing a Validyne DP-45 differential to sense the respiratory-induced pressure drop across a five layer 400 mesh stainless steel screen. Intraesophageal pressure was measured with a Statham P23DC fluid-filled transducer with PE-90 tubing serving as an esophageal cannula. Transducers were coupled via Validyne carrier demodulators to a Buxco Model 6 Pulmonary Mechanics Analyzer which electronically integrates the airflow signal to yield tidal and minute volumes. The analyzer computed total pulmonary resistance, $R_{in/ex}$, at points of equal volume, and dynamic compliance, $C_{dyn}$, at points of zero air flow, according to published methods (Amdur).

Drug aerosols were administered to the animals by a Pulmosonic Nebulizer inserted between a respirator and a solenoid-operated valve at the tracheal cannula. The respirator was adjusted to produce a stroke volume of 2 ml/100 gm body weight at 60 breaths per minute. Activation of the solenoid valve closes normal breathing path to room air, and opens the path to the nebulizer, affecting controlled aerosol delivery. Bronchodilator aerosols were administered for 2 minutes. Histamine aerosols were administered for 15 secs, producing transient, asthma-like bronchoconstriction.

Terbutaline sulfate was obtained from USP Reference Standard (Rockville, Md.), and formulated as a 0.005% solution in 0.9% saline (free drug) or in a liposomal formulation containing about 5 mg drug per 40 $\mu$mole lipid. The liposomes contained egg PC, egg PG, cholesterol, 5:4:1 in phosphate buffered saline, at a final lipid concentration of about 40 $\mu$mol total lipid/ml. The liposome preparation was stored at refrigerator temperature as a concentrate and diluted before use. The total amount of drug present in the concentrate was determined by drug extraction from the mixture and spectrophotometric analysis of the extracted drug in the presence of p-nitroaniline solution (6). The liposome concentrate was then diluted with PBS to give a final drug concentration of 0.005% by weight solution.

Salbutamol sulfate was obtained from ACIC Ltd. (Toronto, Canada), and formulated to a concentration of about 0.001% in 0.9% saline (free drug) or in liposomes prepared as above, and containing a final drug concentration of about $\mu$g/$\mu$mole lipid. The liposomes were stored, diluted, assayed for drug concentration, and diluted to a final drug concentration of about 0.001% by weight, substantially as above.

Histamine diphosphate was obtained from Sigma Chem Co. (St. Louis, Mo.) and dissolved in normal saline to 0.05% by weight.

Terbutaline or salbutamol in free or liposomal form were administered by inhalation, as above, with each animal receiving a total of about 15 $\mu$g/g body weight terbutaline or 1.5 $\mu$g/g body weight salbutamol in a total inhalation volume of about 2 ml. Liquid aerosols of histamine sufficient to produce transient bronchoconstriction were administered via the endotracheal tube, at 15, 45, 75, and 105 minutes after administration of the bronchodilator. Airflow resistance and compliance values were determined shortly after each histamine treatment. The percent increase in resistance was calculated as the difference between the resistance after histamine administration minus baseline resistance value, divided by baseline value. Similarly, the decrease in lung compliance was calculated as the difference between the compliance after histamine administration minus baseline compliance value, divided by baseline value.

The resistance and compliance values at increasing times after terbutaline administration in free (open squares) and liposomal (crosses) form are shown in FIGS. 5A and 5B, respectively. FIGS. 6A and 6B show analogous data for salbutamol drug administration. The data demonstrate the ability of liposomes to enhance protection against bronchoconstriction, at times between about 1–2 hours after drug administration, relative free-drug administration, as discussed above.

While preferred embodiments of the invention have been described herein, it will be appreciated that various changes and modifications may be made without departing from the invention.

It is claimed:

1. A method of treating bronchial constriction, comprising
   providing a liposome composition containing a $\beta_2$-adrenoreceptor agonist drug in liposome-encapsulated form,
   aerosolizing, in a form suitable for inhalation, a metered quantity of the liposome composition containing a $\beta_2$-adrenoreceptor drug in liposome-entrapped form, and
   delivering the metered quantity of liposome composition to the respiratory tract in a liposome aerosol form to produce (a) substantially the same degree of short-term bronchodilation, (b) substantially longer-term effective bronchodilation, and (c) substantially reduced systemic uptake side effects when compared with the administration of the same drug in free-drug form.

2. The method of claim 1, for achieving a selected rate of release of the β-2-agonist drug into the bloodstream when the liposome composition is delivered to the respiratory tract, wherein the liposomes provided in the composition are composed predominantly of phospholipids whose transition temperatures are such as to produce a selected drug release rate into the bloodstream.

3. The method of claim 1, wherein the liposome composition is provided in a liposome paste form in which more than 50% of the aqueous phase is encapsulated within the liposomes, and which further includes mixing the paste with at least 1-2 volumes of the aqueous medium immediately before said aerosolizing.

4. The method of claim 1, wherein the liposome composition provided includes a suspension of spray-dried liposomes in a propellant solvent, and said aerosolizing includes releasing a metered amount of the suspension through a valve from a pressurized container.

5. The method of claim 4, wherein the propellant is selected from the group consisting of $CCl_2F_2$, $CClF_2CClF_2$, and $CClF_2CF_3$.

6. The system of claim 1, wherein the drug is selected from the group consisting of metaproteranol, terbutaline, salbutamol, ephidrine, isoetharine, isoproteranol, procaterol, and bitolterol, and pharmacologically acceptable salts thereof.

7. A method of treating bronchial constriction, comprising
providing a liposome composition containing a beta-2-adrenoreceptor agonist drug in liposome-encapsulated form, said beta-2-adrenoreceptor selected from the group consisting of metaproteranol and pharmacologically acceptable salts thereof,
aerosolizing, in a form suitable for inhalation, a metered quantity of the liposome composition containing said beta-2-adrenoreceptor agonist drug in liposome-encapsulated form, and
delivering the metered quantity of liposome composition to the respiratory tract in a liposome aerosol form to produce (a) substantially the same degree of short-term bronchodilation, (b) substantially longer-term effective bronchodilation, and (c) substantially reduced systemic uptake side effects when compared with administration of the same drug in free-drug form.

* * * * *